United States Patent
Li

(10) Patent No.: US 8,785,719 B2
(45) Date of Patent: Jul. 22, 2014

(54) METHOD FOR CONSTITUTION AND PRODUCTION OF MULTI-GENOTYPE COLONY VARIETIES IN CROP PLANTS

(75) Inventor: Xiaofang Li, Guangzhou (CN)

(73) Assignee: Xiaofang Li, Guangzhou, Guangdong (CN)

( * ) Notice: Subject to any disclaimer, the term of this patent is extended or adjusted under 35 U.S.C. 154(b) by 1725 days.

(21) Appl. No.: 11/993,844

(22) PCT Filed: Jun. 29, 2005

(86) PCT No.: PCT/CN2005/000944
§ 371 (c)(1), (2), (4) Date: Mar. 10, 2010

(87) PCT Pub. No.: WO2007/000080
PCT Pub. Date: Jan. 4, 2007

(65) Prior Publication Data
US 2010/0192242 A1    Jul. 29, 2010

(51) Int. Cl.
*A01H 1/00* (2006.01)
*A01H 5/10* (2006.01)
*A01H 4/00* (2006.01)

(52) U.S. Cl.
USPC ........................................................ 800/260

(58) Field of Classification Search
CPC .................. A01H 5/10; A01H 5/00
USPC ........................................................ 800/260
See application file for complete search history.

(56) References Cited

FOREIGN PATENT DOCUMENTS

| | | |
|---|---|---|
| CN | 1505924 A | 6/2004 |
| CN | 1568663 A | 1/2005 |
| CN | 1568665 A | 1/2005 |
| WO | 2005/102032 A1 | 11/2005 |

OTHER PUBLICATIONS

Probst (Agronomy Journal 49(3): 148-150, 1956).*
Branch (Convergent crossing for peanuts. In Proceedings of peanut breeding symposium, American peanut research and education society, Richmond, VA, Jul. 1981, pp. 18-20).*
Li et al., Development and Evaluation of Multi-genotype Varieties of Rice derived from MAGIC lines, Euphytica (2013) 192:77-86.*
Mott et al., A Method for Fine Mapping Quantitative Trait Loci in Outbred Animal Stocks, PNAS (Proc. Natl. Acad. Sci), Nov. 7, 2000, vol. 97, No. 23, 12649-12654.*
Darvasi and Soller, Advanced Intercross Lines, an Experimental Population for Fine Genetic Mapping, Genetics 141: 1199-1207, Nov. 1995.*
Cavanagh et al., From Mutations to MAGIC: Resources for Gene Discovery, Validation and Delivery in Crop Plants, Current Opinion in Plant Biology 2008, 11:215-221.*
International Search Report mailed Mar. 16, 2006 for PCT Application No. PCT/CN2005/000944 filed Jun. 29, 2005, 4 pages.

* cited by examiner

*Primary Examiner* — Anne Grunberg
(74) *Attorney, Agent, or Firm* — Morrison & Foerster LLP

(57) ABSTRACT

This invention relates to methods for constitution and production of colony varieties of crops. Its characteristics are shown below. According to their phenotypes, single-genotype varieties, hybrid combinations or mixtures of varieties and combinations from fundamental populations, which are consistent or uniform in major characters and share particular breeding goals, will constitute the colony varieties of crops. The said single-genotype varieties or hybrid combinations are multiplied separately. According to the breeding goals, their seeds are mixed in a specific ratio to form the preparations for planting. The varieties produced in such a way are featured with uniformity, stability and peculiarity.

11 Claims, No Drawings

METHOD FOR CONSTITUTION AND PRODUCTION OF MULTI-GENOTYPE COLONY VARIETIES IN CROP PLANTS

CROSS REFERENCE TO RELATED APPLICATIONS

This application is a U.S. National Phase patent application of PCT/CN2005/000944, filed Jun. 29, 2005, the contents of which are hereby incorporated by reference in the present disclosure in their entirety.

FIELD OF INVENTION

The present invention relates to the breeding method for formation and production of multi-genotype colony varieties in crops, including self-pollinating, frequent-cross-pollinating and asexually propagated plants.

BACKGROUND OF INVENTION

As an example, rice breeding went through two revolutionary breakthroughs of semi-dwarfication and hybrid breeding in history. The semi-dwarfication breeding of rice was first started by Chinese academician Yaoxiang Huang from the Rice Research Institute of Guangdong Academy of Agricultural Sciences of China and breeders in other parts of the world. The hybrid rice breeding was invented by Chinese academician Longping Yuan, 'the father of hybrid rice'. These two events promoted the rice breeding of China to a leading position in the world. Up to now, the production of rice and other crop plants has nevertheless been dominated by single genotype varieties, which share one single genotype for all their plants within a certain variety. The development and release of single-genotype varieties directly resulted in an increasing reduction of genetic diversity. Single-genotype varieties became increasingly narrow in genetic backgrounds and became increasingly weak in the resistance and tolerance to diseases and biological natural enemies, resulting in the prevalence of various diseases in the past, such as rice *helminthosporium* leaf spot, potato blight, wheat strip rust, Southern leaf blight (*Bipolaris maydis*) and Northern leaf blight (*Setosphaeria turcica*) in maize, and recent outbreak of locusts in some African regions. The infall of rust disease of soybean in the United States in 2004 brought about a high panic. According to a report of a meeting for World Cereal Day in 4 Oct., 2004, three fourths of the genes in agricultural plants vanished in the last century, and things are getting still worse at present.

Hybrid rice also belongs to a single genotype category. In addition, the problem of seed impurity in the production and multiplication of hybrid rice would occur more or less every year due to the instability of their sterile lines. A case of example is the complete failure of production of hybrid rice seeds in an around 3000 hectares of lands in Guangdong province of China in 2005. The cause of the failure was the sensibility to cold dew wind due to spraying of giberrelin 920 during hybrid seeds production. Due to its high social and research costs and high technical risks, hybrid rice has not been commercialized in large scale in United States and other countries. In China, the production of hybrid rice has been increasing very fast with the country's rapid development of market-oriented economy. One of the important reasons is that the enforcement of plant variety rights is still incomplete in the country, and in particular, the conventional varieties cannot be well protected. As a result, the seed enterprises are only willing to produce and sell hybrid seeds rather than conventional variety seeds, as they are able to dominate on the seed market through a control of the production of hybrid seeds which is characterized with high cost and risk. The economical interests of seed companies played an important role for extension of hybrid rice. For the heterosis utilization in other crop plants, the cost is also very high for developing sterile lines and making two-line or three-line combinations. The application of chemical emasculation method of hybrid seeds production is badly restricted by climatological factors and other technical problems and it will cause chemical pollution and other environmental problems.

High yielding, high quality and multiple resistances to pests and diseases are always the targets of crop breeding, but it is hard to conciliate these three goals for a single-genotype variety and it is getting increasingly difficult for a single-genotype variety to exceed in all aspects. Briefly speaking, for the traditional crop breeding or single-genotype breeding, breeders attempt to select desirable and perfect individuals and it is unavoidable to attend to one thing and lose another.

The inventor Xiaofang Li has previously created a new breeding strategy for crop plants, which was called multi-genotype (colony variety) breeding or genetic diversity breeding. She has ever applied a patent for it and the application number was PCT/CN2004/000657. The core of this breeding strategy is to create and form an elite group instead of desirable individuals in crop plants. It has made major innovation in the concept, strategy, tactic, selection criteria of breeding in crop plants. It focuses on the coordination in yield, quality and resistance to pests and diseases of crop plants. It will facilitate the active protection and utilization of genetic diversity of crop plants in agriculture. The multi-genotype (colony variety) breeding is a specialized term. Judged by its goal, it can be called genetic diversity breeding. The multi-genotype (colony) variety can be generally called group variety for the sake of farmers in understanding.

The multi-genotype (colony variety) breeding includes the following seven phases. (1) Selection of parental lines: According to the breeding targets, the male and female parents with many excellent agronomical traits or some special characteristics will be chosen. It's unnecessary for a pair of male and female parents to supplement mutually in traits. However, all the parental lines should supplement collectively and the balance in their traits should also be considered for the breeding targets. The parental lines should vary according to the breeding goal. For instance, more parental lines with high quality should be chosen for quality breeding, and more resistant parental lines should be adopted for resistance and tolerance breeding. (2) Hybridization: Maximum number of recombinants should be created at the minimum cost of hybridization. For instance, composite or piled-up hybridization, in which pairs of parental lines are crossed for the first time and pairs of F1 are subsequently crossed once more, will greatly reduce the workload of hybridization and large quantity of recombinants can be acquired in a short time. (3) Self-crossing for segregation and recombination: It can be easily realized for self-pollinating or often-cross-pollinating crop plants. In this phase, all family lines of hybridization should be retained possibly and certain number of plants should be kept for each family line according to the multiplication capability of the plants. A single-seed-descent selection should be conducted for all family lines. Each family line should not be totally eliminated too early so that the genetic diversity can be maintained in all these family lines. According to breeder's experience, the poor plants can be deleted from a family line after several generations of self-crossing. (4) Characterization of individual plant lines: After all family lines become stable, each individual plant line will be evaluated for selection. After the poor plant lines are eliminated, the other plant lines will constitute the fundamental population and their major characteristics will be determined or measured. The indices to be investigated will depend on facilities and time allowance. The growth duration and plant height must be investigated, for they indicate the uniformity of a variety. (5) Grouping and assortment: The data for characteristics in the fundamental population are put in the computers for analysis. The individual plant lines which are identical in growth duration and plant height and share a common breeding goal are merged in a group to become a colony variety. Couples or even dozens of colony varieties can be developed from a fundamental population according to growth duration, plant height and breeding goals. (6) Improvement of colony varieties: The individual plant lines of a colony variety are grown in separate rows in the same plot of a field to examine the data for accuracy in measurement or computer input. The inconsistent plant lines or lines with obvious inaccuracy in data are deleted to ensure a whole uniformity in a plot. This process can be repeated for more than one generation for a multilevel improvement of a colony variety. (7) Formation of multi-genotype colony varieties: The original plant lines of a colony variety in the fundamental population can be regarded as breeder seed. Their corresponding plant lines are multiplied separately and their seeds are mixed in a specific ratio to form a multi-genotype colony variety or group variety. Then normal regional trials like that for conventional breeding are conducted subsequently. The seeds of the fundamental population formed in the fourth phase are equivalent to breeder seeds, and those of the original plant lines formed in the sixth phase are the stock seeds of colony varieties. As individual plant lines are different in their multiplication capacity, farmers won't be able to reserve the seeds for planting for a long time. The seeds companies will be able to produce the seeds properly and keep their plants stable and unchangeable in characteristics. In case farmers reserve the seeds for planting temporally, serious risk of sterility caused by sterile lines won't take place. For those crop plants which are easy in hybrid seed production with no need of sterile lines, the hybrid $F_1$ can be used as fundamental populations and multi-genotype hybrid combinations or a mixture of colony variety and combination can be constructed from them. Figuratively speaking, conventional single-genotype breeding tends to be a process of selecting beauideal individuals while multi-genotype breeding is a course to seek an elite group.

The main advantage of genetic diversity breeding is that it is as easy as conventional breeding in technical difficulty but its cost for seed production is much lower than hybrid combinations. In addition, it avoids the risk of sterility caused by sterile lines. Thus it is a low-cost and zero-risk technology. This technology can be effectively protected by law through application of patent and the interests of seed enterprises can be also guaranteed. It can promote the industrialization of seeds of crop plants and enhance the core competitiveness in agriculture. Right now, the protection of bio-diversity is a hot topic and focus of public attention around the world. This technology will also boost the protection of bio-diversity and promote the sustainable development in agriculture.

DETAILED DESCRIPTION OF THE INVENTION

According to the breeding targets, the male and female parents with many excellent agronomical traits or some special characteristics will be chosen and the number of parents could vary accordingly. Various types of hybridizations are conducted between pairs of parental lines. Maximum number of recombinants should be created at the minimum cost of hybridization. After self-crossing for several generations, the progenies of hybrids of self-pollinating crop plants will undergo genetic segregation and recombination until they become stable in both genotype and phenotype and finally form the fundamental population of multi-genotype breeding. For heterosis utilization of cross-pollinating crop plants, the F1 hybrids will be the basic elements of colony varieties and fundamental populations. For asexually-propagated crop plants, the stable genotypes of recombinants of hybrid $F_1$ generation can be retained directly. In the above course, more individual plant lines should be retained as far as possible so that the maximum genetic diversity of them could be maintained. Subsequently, each individual plant line in the fundamental population will be planted again, their agronomical characteristics will be measured or examined, and selection will be made from them. They will be sorted on computer according to their qualitative and quantitative traits. All individual lines with the same breeding goals, identical commodity attributes (such as growth duration and plant type) and some special traits of breeding purpose will be incorporated into a colony. In the meantime, the original individual lines should also be retained separately. The individual lines in the same colony will be grown in the same plot of field to check the consistency in performance and examine the accuracy of collected data. Such a process can go on for several rounds to fulfill multi-level improvement of a colony.

After the fundamental individual plant lines are decided for a colony, the seeds of each line will be mixed equally or in a certain ratio to form a specific multi-genotype variety. As each individual plant line in a colony variety is different in multiplication capacity, farmers won't be able to reserve the seeds for planting for many times. This will be in favor of the sale of seeds companies because only they are able to reproduce expertly the seeds of individual lines of original plants and make the elite colony varieties keep unchanged in characteristics. This invention patent provides protection for the production or origination of fundamental population (i.e. original plant lines) of colony varieties in crop plants and the manner of their seed production. This invention provides the method for constitution of multi-genotype colony varieties in crop plants. It also contains the method for production of seeds of colony varieties. Through these two methods, multi-genotype colony varieties that are featured with uniformity, stability and peculiarity can be developed and the desired breeding goals in quality, yield and resistance to pests and diseases can be fulfilled.

This invention relates to methods for constitution and production of colony varieties of crops. Its characteristics are shown as below. According to their phenotypes, single-genotype varieties from fundamental populations, which are consistent or uniform in major characters and share particular breeding goals, are matched to form the colony varieties of crops. The said single-genotype varieties or hybrid combinations are multiplied separately. According to the breeding goals, their seeds are mixed in a specific ratio to form the preparations for planting.

The said single-genotype varieties are the single-genotype breeding lines selected from descendants of single crosses, double crosses, triple crosses, composite crosses, or back crosses according to their plant type and growth duration.

The said crops include self-pollinating, often-cross-pollinating and asexually-propagated crop plants. The said self-pollinating crops include rice, peanut, wheat, soybean or tomato, etc. The said often-cross-pollinating crops include rape, cotton, chili pepper, flowering Chinese cabbage (*Brassica campestris* L. ssp. *Chinensis* var. *utilis* Tsen, et, Lee), eggplant or cabbage mustard, etc. The said asexually-propagated crops include potato, sweet potato, pitahaya, rose or camellia, etc.

The content of invention is elucidated in detail as below.

I. Constitution of Single-Genotype Fundamental Population

1. To utilize various crossing manners: composite crossing [(A×B)×(C×D)]×[(E×F)×(J×H)], single crossing (A×B), double crossing (A×B)×(C×D), triple crossing (A×B)×C, backcrossing (A×B)×A, where A is the recurrent parental line and it can be conducted for 2-10 times. The stable descendants of single genotype produced in above-mentioned crossing manners or hybrid combinations, will constitute the fundamental populations.

2. To utilize various gene introgression lines: (A×B)×A; (A×C)×A; (A×D)×A; (A×E)×A; (A×F)×A; (A×J)×A; (A×H)×A; (A×I)×A, where A is the parental line of gene receptor, B, C, D, E, F, J, H, I, are the parental lines of various gene donors respectively. The number of parental lines of gene donors is two to 5000 and the backcross sing with A can be conducted for 2-10 times. The stable single-genotype descendants of the said introgression lines or hybrid combinations will constitute the fundamental populations.

3. Stable single-genotype descendants of half-sibling or full-sibling recurrent selection or hybrid combinations will constitute the fundamental populations.

4. Part or all of the stable single-genotype varieties or hybrid combinations produced by methods 1-3 are adopted as fundamental populations.

5. Part or all of stable single-genotype varieties or hybrid combinations in various fundamental populations produced by methods 1-4 are adopted as fundamental populations.

6. Asexually reproductive clone lines produced by methods 1-5 are adopted as fundamental populations.

7. The number of parental lines to be used for construction of fundamental populations ranges from 2 to 10000.

8. Each colony variety may contain 2-10000 single-genotype varieties or combinations.

II. Manner of Seed Production of Colony Varieties

The single-genotype varieties or combinations in the fundamental populations, which are produced by the above-mentioned methods, are multiplied separately. According to breeding goals, their seeds are mixed in specific ratios to become the multi-genotype colony varieties or group varieties. Each colony variety or group variety may contain 2-10000 single-genotype varieties or hybrid combinations.

III. Technique for Seed Examination

The colony varieties developed by genetic diversity breeding contain a multitude of genotypes. The seeds of this type of variety will also contain all the genotypes of its components and they will display genetic diversity and heterogeneity at molecular level. After the seeds are mixed fully, some of them will be randomly sampled for molecular detection. The difference in SSR, RAPD and other molecular markers will be detected in single-grain samples and their difference should fall within the range of breeder seeds in the fundamental populations. The blood relationship between them should also fall within the range of parental lines adopted in hybridization. The genetic diversity and molecular heterogeneity won't be detected in the seed or plant samples of single-genotype varieties or hybrid combinations.

Embodiments of the Invention

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scopes of the invention. Thus these samples are just illustrations of the invention and they won't confine the scope of its application.

Example 1

Constitution of Fundamental Populations from Descendants of Composite Hybridizations and their Seed Production I. Experimental Material—Rice 12 parental plants with different origins were used in the experiment. Eight double-cropping varieties in South China were included: Zhong-Er-Ruan-Zhan, Yue-Hua-Zhan, Yue-Tai-Zhan and Er-Ba-Zhan are high grain-quality varieties, which are developed by the Rice Research Institute of Guangdong Academy of Agricultural Science (RRI of GAAS) in China; Feng-Ai-Zhan and Yue-Xiang-Zhan are high-yielding varieties also developed by RRI of GAAS; Qi-Gui-Zao and Te-Xian-Zhan 13 are high-yielding varieties developed by the Foshan Agricultural Research Institute in Guangdong province of China. Duo-Kang 578, Duo-Kang 580 and Duo-Kang 583 are disease-resistant varieties introduced from the International Rice Research Institute in the Philippines. Lemont is a famous high grain-quality variety in the U.S.A. Yue-Xiang-Zhan, the control in the experiment, has been the check variety for the rice regional trials in China and in Guangdong province up to now.

II. Method for Constitution of Fundamental Populations

The first hybridization included the following six separate crosses:

| | |
|---|---|
| Feng-Ai-Zhan × Duo-Kang 578, | Lemont × Zhong-Er-Ruan-Zhan, |
| Yue-Tai-Zhan × Duo-Kang 580, | Yue-Hua-Zhan × Er-Ba-Zhan, |
| Te-Xian-Zhan 13 × Yue-Xiang-Zhan, | Qi-Gui-Zao × Duo-Kang 583. |

The secondary hybridization involved simple crosses between the male and female of the F1 generation. As the hybridization was performed in non-segregation generations, the work of hybridization was not great and only more than 50 seeds were surely produced. The crosses are listed below:

(Feng-Ai-Zhan×Duo-Kang 578)×(Lemont×Zhong-Er-Ruan-Zhan), (Yue-Tai-Zhan×Duo-Kang 580)×(Yue-Hua-Zhan×Er-Ba-Zhan), (Te-Xian-Zhan13×Yue-Xiang-Zhan)×(Qi-Gui-Zao×Duo-Kang 583).

The tertiary hybridization was below:

[(Feng-Ai-Zhan×Duo-Kang 578)×(Lemont×Er-Ruan-Zhan)]—female×{[(Yue-Tai-Zhan×Duo-Kang 580)×(Yue-Hua-Zhan×Er-Ba-Zhan)]—male 1+[(Te Xian Zhan 13×Yue Xiang Zhan)×(Qi Gui Zao×Duo Kang 583)]—male 2}.

Note: in the above notations of crosses, the female is placed in front and the male in back.

First, each individual plant of the female population was numbered and so was that of the two male populations. The plants in the female population were then fertilized with the mixed pollens of plants in the two male populations, both of which had the same plant numbers of the corresponding female plants. In total, 500 hybrids have been produced. For the progenies of the 500 hybrids, at least 10 self-crossed plants were retained for each individual plant line, and they were self-crossed for several generations towards their stability. From about 5000 stable individual plants, 2000 elite individual plants were chosen to form the fundamental populations and they were numbered as SD1, SD2, SD3, SD4, . . . SD2000.

III. Method for Constitution of Colony Varieties and Seed Production

After evaluation of the fundamental population, 32 single-genotype lines with consistent growth duration and plant height and high grain quality were selected. After they were planted once more in the field for confirming their performance, they made up the colony variety or group variety JTSD. It included the following components: SD1, SD17, SD18 (strong resistance), SD24, SD31, SD44, SD51, SD57, SD88 (strong resistance), SD89 (soft cooked rice), SD143, SD247, SD354 (hard cooked rice), SD460 (soft cooked rice), SD567, SD673, SD776 (soft cooked rice), SD890, SD909 (soft cooked rice), SD996, SD1097 (hard cooked rice), SD1112, SD1210 (strong resistance), SD1213, SD1322 (hard cooked rice), SD1428 (strong resistance), SD1533, SD1634, SD1702, SD1803, SD1908, SD1914.

Performance of colony variety JTSD: Days from seeding to heading was 80 days, plant height at heading was 65 cm, days from seeding to maturity was 115 days, plant height at maturity was 91 cm. Amylose content was 19%, arriving at the first grade of state standard in China for grain quality of India rice. The yield equivalent was 480 Kg/667 m$^2$, increasing 5% over other common varieties of the same grain quality.

Method for Seed Production

1. The above-mentioned 32 plant lines were multiplied separately and their seeds were then mixed in an equal ratio to form preparations for planting.

2. For harder cooked rice, the amount of seeds of plant lines with hard cooked rice should be increased moderately, or the amount of seeds of plant lines with soft cooked rice would be reduced.

3. If a colony variety is grown in areas with serious diseases, the amount of seeds of plant lines with strong disease resistance should be increased for better resistance.

4. The ratio of mixing can be modified according to a special requirement for certain characteristics. For retaining stability of colony varieties in characteristics, the modified amount and adjusted ratio should be recorded accurately and strictly, so that identical colony varieties can be produced in a same way in the next preparation of seeds.

5. Other colony varieties with some special characteristics or particular breeding goals can be developed from the fundamental population in a similar way as mentioned above. Scores, dozens or even hundreds of colony or group varieties with distinctive characteristics can be developed from a fundamental population.

6. The original plant lines of a colony variety in the fundamental population will be checked for identification and verification of seeds in the seed production.

Example 2

Constitution of Fundamental Populations from Descendants of Single-Cross Hybridizations and their Seed Production I. Experimental Material—Soybean Six parental lines of different origins were adopted in the experiment: Ken-Nong 18, Ji-Yu 47, Liao-Dou 1, He-Feng 41, Ji-Yu 58 and Liao-Dou 13.

II. Method for Constitution of Fundamental Populations Ken-Nong 18×Ji-Yu 47, 500 Seeds were Collected.

Liao-Dou 1×He-Feng 41, 400 seeds were collected. Ji-Yu 58×Liao-Dou 13, 700 seeds were collected.

The seeds collected in the single-cross hybridization were all sowed in the field to acquire 1600 individual plants. In the next generation, 10 plants were grown in a row for each plant line and a total of 1600 rows were planted for all plant lines. Two seeds were collected from each plant. In later generations, at least 10 self-crossed plants were retained for each individual plant line, and they were self-crossed for several generations towards their stability. From about 16000 stable individual plants, 4000 elite plants were chosen to form the fundamental populations and they were numbered as DD1, DD2, DD3, DD4 . . . DD4000.

III. Method for Constitution of Colony Varieties and Seed Production

After evaluation of the fundamental population, 40 single-genotype lines with consistent growth duration and plant height and with high quality were selected. After they were planted once more in the field for confirming their performance, they made up the colony variety or group variety JTDD. It included the following plant lines: DD1, DD18 (strong resistance), DD31, DD44, DD57, DD59, DD88 (strong resistance), DD143, DD247, DD354 (high oil content), DD460 (high protein content), DD567, DD776 (high protein content), DD909 (high protein content), DD996, DD1044, DD1097 (high oil content), DD1112, DD1210 (strong resistance), DD1213, DD1322 (high oil content), DD1428 (strong resistance), DD1634, DD1702, DD1843, DD1914, DD2017, DD2047, DD2473, DD2533, DD2551, DD2688 (strong resistance), DD2908, DD3051, DD3289 (high protein content), DD3524, DD3803, DD3890, DD3954 (high oil content) and DD3989 (high protein content).

Performance of colony variety JTDD: Growth duration was 124 days, plant height was 105 cm, crude protein content was 45% and oil content was 20%.

Method for Seed Production

1. The above-mentioned 40 plant lines were multiplied separately, and then their seeds were mixed in an equal ratio to form the preparation for next planting.

2. For high protein or oil content, the amount of seeds of plant lines with high protein or oil content should be increased moderately.

3. If a colony variety is grown in areas with serious diseases, the amount of seeds of plant lines with strong disease resistance should be increased for better resistance.

4. The ratio of mixing can be modified according to a special requirement for certain characteristics. For stability of colony varieties in characteristics, the modified amount and adjusted ratio should be recorded accurately and strictly, so that identical colony varieties can be produced in a same way in the next preparation of seeds.

5. Other colony varieties with some special characteristics or particular breeding goals can be developed from the fundamental population in a similar way as mentioned above. Scores, dozens or even hundreds of colony or group varieties with distinctive characteristics can be developed from a fundamental population.

6. The original plant lines of a colony variety in the fundamental population will be checked for identification and verification of seeds in the seed production.

Example 3

Constitution of Fundamental Populations from Descendants of Double-Cross Hybridizations and their Seed Production I. Experimental Material—Rape Intensified breeding of comprehensively-chosen high-erucil acid-content varieties—Below are the parental lines of crosses: 4 varieties of Mercury, Neptune, Castor and R-588 with a high erucil acid content of more than 53% (introduced from Canada), Indore (introduced from USA); two 'dual-high' varieties in China S87-2127 and S87-2365; three high-linoleic acid and high linolenic acid varieties in China, Zhong-You 821 (by Oil plants Research Institute, Chinese Academy of Agricultural Sciences), Ning-You 7 (by Jiangsu Academy of Agricultural Sciences), Wang-You 17 (from Hubei); Low-thioglycoside variety Wan-You 6 (by Anhui Academy of Agricultural Sciences); introduced 'dual-high' variety Gotarshiji. Hybridization was conducted between pairs of the above varieties.

II. Method for Constitution of Fundamental Populations

The first hybridization:

Mercury×S87-2127; Neptune×S87-2365; Castor×Zhong-You 821; Indore×Ning-You 7; Gotarshiji×Wang-You 17; R-588×Wan-You 6.

The secondary hybridization:

(Mercury×S87-2127)×(Neptune×S87-2365), 78 seeds were collected. (Castor×Zhong-You 821)×(Indore×Ning-You 7), 70 seeds were collected. (Gotarshiji×Wang-You 17)×(R-588×Wan-You 6), 70 seeds were collected.

A total of 218 hybrids were obtained from above three double-cross hybridizations. In the next generation, 10 plants were grown in a row for each plant line and a total of 2180 rows were planted for all plant lines. Two seeds were collected from each plant. In later generations, at least 10 self-crossed plants were retained for each individual plant line, and they were self-crossed for several generations towards their stability. For all these plant lines, a routine roguing could be performed until they became stable and uniform. The single-genotype plant lines in the fundamental population were numbered as YC1, YC2, YC3, YC4 . . . YC2180.

III. Method for Constitution of Colony Varieties and Seed Production

After evaluation of the fundamental population, 27ingle-genotype lines with good comprehensive characters, consistent growth durations, low erucil acid content and high oil content were selected from 2180 plant lines of the fundamental population. After they were planted once more in the field for confirming their performance, they made up the colony variety or group variety JTYC. It included the following plant lines: YC2, YC17 (strong resistance), YC33, YC45, YC56, YC58, YC89 (strong resistance), YC145, YC237, YC344 (high oil content), YC466 (high erucil acid content), YC569, YC776 (high erucil acid content), YC909 (high erucil acid content), YC996, YC1044, YC1097 (high oil content), YC1112, YC1210 (strong resistance), YC1213, YC1322 (high oil content), YC1428 (strong resistance), YC1634, YC1702, YC1843, YC1914, YC2017 and YC2047.

Performance of colony variety JTYC: Growth duration 220 days, plant height 150 cm, oil content 48%, erucil acid content 42%.

Method for Seed Production

1. The above-mentioned 27 plant lines were multiplied separately and their seeds were then mixed in an equal ratio to form the preparation for next planting.
2. For industrial use with high oil and erucil acid contents, the amount of seeds of plant lines with high oil and erucil acid contents should be increased moderately.
3. If a colony variety is grown in areas with serious diseases, the amount of seeds of plant lines with strong disease resistance should be increased for better resistance.
4. The ratio of mixing can be modified according to a special requirement for certain characteristics. For stability of colony varieties in characteristics, the modified amount and adjusted ratio should be recorded accurately and strictly, so that identical colony varieties can be produced in a same way in the next preparation of seeds.
5. Other colony varieties with some special characteristics or particular breeding goals can be developed from the fundamental population in a similar way as mentioned above. Scores, dozens or even hundreds of colony or group varieties with distinctive characteristics can be developed from a fundamental population.
6. The original plant lines of a colony variety in the fundamental population will be checked for identification and verification of seeds in the seed production.

Example 4

Constitution of Fundamental Populations from Descendants of Triple-Cross Hybridizations and their Seed Production I. Experimental Material—Peanut Six parental lines of various origins were included in the hybridizations: Pu-Hua 6, Hua-Xuan 1, Xu-Hua 6, Shan-You 321, Yue-You 79, and FU91-103.

II. Method for Constitution of Fundamental Populations (Shan-You 321×Yue-You 79)×FU91-103, 500 stable individual plant lines produced from the descendants of the hybridization; (Hua-Xuan 1×Xu-Hua 6)×Shan-You 321, 600 stable individual plant lines produced from the descendants of the hybridization. These plant lines made up the fundamental lines and they were numbered as HS1, HS2, HS3, HS4 . . . HS1100.

III. Method for Constitution of Colony Varieties and Seed Production

Low yield is a major limiting factor for the conventional varieties of peanut, and protein content is lower than 32% for most peanut varieties, with only 5% of varieties having a protein content of more than 32%. Through screening and sorting, one colony variety JTHS were developed according to the dates of flowering and maturity and plant height at pegging and maturity of individual lines of the colony. The selection was conducted with the protein content as the major index. As it belongs to a self-pollinating plant, its stability would remain unchanged during multiplication.

The colony variety JTHS included the following 15 individual plant lines of the fundamental population: HS2, HS27, HS88, HS139 (good resistance), HS231, HS247, HS354 (good resistance), HS440, HS460, HS511 (good resistance), HS567, HS578, HS886, HS897 and HS1043.

Performance of colony variety JTHS: Growth duration 130 days; plant height at maturity 110 cm; yield equivalent 356 Kg/667 m², a 27% increase over the control; protein content 33%.

Method for Seed Production

1. The above-mentioned 15 plant lines were multiplied separately and their seeds were then mixed in an equal ratio to form the preparation for next planting.
2. If a colony variety is grown in areas with serious diseases, the amount of seeds of plant lines with strong disease resistance should be increased for better resistance.
3. The ratio of mixing can be modified according to a special requirement for certain characteristics. For stability of colony varieties in characteristics, the modified amount and adjusted ratio should be recorded accurately and strictly, so that identical colony varieties can be produced in a same way in the next preparation of seeds.
4. Other colony varieties with some special characteristics or particular breeding goals can be developed from the fundamental population in a similar way as mentioned above. Scores, dozens or even hundreds of colony or group varieties with distinctive characteristics can be developed from a fundamental population.
5. The original plant lines of a colony variety in the fundamental population will be checked for identification and verification of seeds in the seed production.

Example 5

Constitution of Fundamental Populations from Descendants of Back-Cross Hybridizations and their Seed Production I. Experimental Materials—Cotton 6 parental lines of different origins were utilized in the experiment: Zhong-Mian-Suo 24, Zhong-Mian-Suo 35, Zhong-Mian-Suo 36, Zhong-Mian-Suo 19, Yu-Mian 19, Han-Dan 284. Each line was back-crossed with one of the following six hybridizations.

II. Method for Constitution of Fundamental Populations (Zhong-Mian-Suo 24×Zhong-Mian-Suo 35)×Zhong-Mian-Suo 24, 100 seeds were collected; (Zhong-Mian-Suo 35×Zhong-Mian-Suo 19)×Zhong-Mian-Suo 35, 100 seeds were collected; (Zhong-Mian-Suo 19×Zhong-Mian-Suo 36)×Zhong-Mian-Suo 19, 100 seeds were collected; (Zhong-Mian-Suo 36×Yu-Mian 19)×Zhong-Mian-Suo 36, 100 seeds were collected; (Yu-Mian 19×Han-Dan 284)×Yu-Mian 19, 100 seeds were collected; (Han-Dan 284×Zhong-Mian-Suo 24)×Han-Dan 284, 100 seeds were collected.

The seeds collected in the back-cross hybridization were all sowed in the field to acquire 1000 individual plants. In the next generation, 10 plants were grown in a row for each plant line and a total of 1000 rows were planted for all plant lines. Two seeds were collected from each plant. In later generations, at least 10 self-crossed plants were retained for each individual plant line, and they were self-crossed for several generations towards their stability. From about 10000 stable individual plants, 3000 elite plants were chosen to form the fundamental populations and they were numbered as MH1, MH2, MH3, MH4, . . . MH3000.

III. Method for Constitution of Colony Varieties and Seed Production

After evaluation of the fundamental population, 33 single-genotype lines with consistent plant height and good fiber quality were selected from 3000 plant lines of the fundamental population and they made up the colony variety or group variety JTMH. It included the following plant lines: MH1, MH18 (good resistance), MH31, MH44, MH57, MH59, MH88 (good resistance), MH143, MH247, MH354 (high fiber strength), MH460 (long fiber), MH567, MH776 (long fiber), MH909 (long fiber), MH996, MH1044, MH1097 (high fiber strength), MH1112, MH1210 (good resistance), MH1213, MH1322 (high fiber strength), MH1428 (good resistance), MH1634, MH1702, MH1843, MH1914, MH2017, MH2047, MH2473, MH2533, MH2551, MH2688 (good resistance) and MH2908.

Performance of colony variety JTMH: Growth duration 114 days; plant height 98 cm; fiber length 24 mm, fiber strength 4 g.

Method for Seed Production

1. The above-mentioned 33 plant lines were multiplied separately and their seeds were then mixed in an equal ratio to form the preparation for next planting.
2. For high fiber strength or length, the amount of seeds of plant lines with high fiber strength or length should be increased moderately.
3. If a colony variety is grown in areas with serious diseases, the amount of seeds of plant lines with strong disease resistance should be increased for better resistance.
4. The ratio of mixing can be modified according to a special requirement for certain characteristics. For stability of colony varieties in characteristics, the modified amount and adjusted ratio should be recorded accurately and strictly, so that identical colony varieties can be produced in a same way in the next preparation of seeds.
5. Other colony varieties with some special characteristics or particular breeding goals can be developed from the fundamental population in a similar way as mentioned above. Scores, dozens or even hundreds of colony or group varieties with distinctive characteristics can be developed from a fundamental population.
6. The original plant lines of a colony variety in the fundamental population will be checked for identification and verification of seeds in the seed production.

Example 6

Constitution of Fundamental Populations from Descendants of Gene Introgression Lines and their Seed Production I. Experimental Materials—Tomato 17 varieties of various origins were adopted as parental lines: Ying-Shi-Da-Hong, Fen-Hong D-80, Bo-Yu 368, Bo-Yu 367, Jin-Xiang-Fan-Zao, Jin-Xiang-Fan-Bao, Jia-Fen 17, Fan-Qie-Dong-Nong 704, Fan-Qie-Mao-Fen 802, Yu-Fan-Qie 1, Fan-Qie-Zhong-Su 5, Zhong-Za 11, Zhong-Za 9, Hong-Za 18, Hong-Za 10, Fan-Qie-Xi-Fen 3, Fen-Hong D-80. Ying-Shi-Da-Hong was used as recipient and recurrent line and other 16 varieties were used as donor lines.

II. Method for Constitution of Fundamental Populations (Ying-Shi-Da-Hong×Fen-Hong D-80)×Ying-Shi-Da-Hong, 100 seeds were collected.

(Ying-Shi-Da-Hong×Bo-Yu 368)×Ying-Shi-Da-Hong, 100 seeds were collected.

(Ying-Shi-Da-Hong×Bo-Yu 367)×Ying-Shi-Da-Hong, 100 seeds were collected.

(Ying-Shi-Da-Hong×Jin-Xiang-Fan-Zao)×Ying-Shi-Da-Hong, 100 seeds were collected.

(Ying-Shi-Da-Hong×Jin-Xiang-Fan-Bao)×Ying-Shi-Da-Hong, 100 seeds were collected.

(Ying-Shi-Da-Hong×Jia-Fen 17)×Ying-Shi-Da-Hong, 100 seeds were collected.

(Ying-Shi-Da-Hong×Fan-Qie-Dong-Nong 704)×Ying-Shi-Da-Hong, 100 seeds were collected.

(Ying-Shi-Da-Hong×Fan-Qie-Mao-Fen 802)×Ying-Shi-Da-Hong, 100 seeds were collected.

(Ying-Shi-Da-Hong×Yu-Fan-Qie 1)×Ying-Shi-Da-Hong, 100 seeds were collected.

(Ying-Shi-Da-Hong×Fan-Qie-Zhong-Su 5)×Ying-Shi-Da-Hong, 100 seeds were collected.

(Ying-Shi-Da-Hong×Zhong-Za 11)×Ying-Shi-Da-Hong, 100 seeds were collected.

(Ying-Shi-Da-Hong×Zhong-Za 9)×Ying-Shi-Da-Hong, 100 seeds were collected.

(Ying-Shi-Da-Hong×Hong-Za 18)×Ying-Shi-Da-Hong, 100 seeds were collected.

(Ying-Shi-Da-Hong×Hong-Za 10)×Ying-Shi-Da-Hong, 100 seeds were collected.

(Ying-Shi-Da-Hong×Fan-Qie-Xi-Fen 3)×Ying-Shi-Da-Hong, 100 seeds were collected.

(Ying-Shi-Da-Hong×Fen-Hong D-80)×Ying-Shi-Da-Hong, 100 seeds were collected.

In these hybridizations, some genes or genetic backgrounds of the 16 various varieties were introduced into the recipient line of Ying-Shi-Da-Hong to create its introgression lines of foreign genes. The introgression lines could also be the descendants of plant lines which were genetically engineered through gene transformation. The back-cross could be conducted for more than one generation. The fundamental populations produced in such a way would be relatively tidy and uniform but their genetic diversity would be reduced some extent. The seeds collected in the above back-cross hybridization were all sowed in the field to acquire 1600 individual plants. In the next generation, 10 plants were grown in a row for each plant line and a total of 1600 rows were planted for all plant lines. Two seeds were collected from each plant. In later generations, at least 10 self-crossed plants were retained for each individual plant line, and they were self-crossed for several generations towards their stability. From about 16000 stable individual plants, 4010 elite individual plants were chosen to form the fundamental populations and they were numbered as FQ1, FQ2, FQ3, FQ4, . . . FQ4010.

III. Method for Constitution of Colony Varieties and Seed Production

After evaluation of the fundamental population, 40 single-genotype lines with consistent plant height and good quality in sweetness were selected from 4010 plant lines of the fundamental population and they made up the colony variety or group variety JTFQ. It included the following plant lines: FQ5, FQ18 (good resistance), FQ41, FQ49, FQ57 (high yielding), FQ59, FQ88 (good resistance), FQ145, FQ247, FQ354 (high solid content), FQ460, FQ567, FQ776 (high yielding), FQ909 (high yielding), FQ986, FQ1043, FQ1097 (high solid content), FQ1112, FQ1210 (good resistance), FQ1213, FQ1322 (high solid content), FQ1428 (good resistance), FQ1634 (high yielding), FQ1702, FQ1843 (good resistance), FQ1914, FQ2017, FQ2047, FQ2473, FQ2533, FQ2551, FQ2688, FQ2908, FQ3051, FQ3289, FQ3524 (high solid content), FQ3803, FQ3890, FQ3954 and FQ4002 (high yielding).

Performance of colony variety JTFQ: Growth duration 94 days; plant height 98 cm; mean individual-fruit weight 250 g.

Method for Seed Production

1. The above-mentioned 40 plant lines were multiplied separately and their seeds were then mixed in an equal ratio to form the preparation for next planting.
2. For heavy fruits or high solid content, the amount of seeds of plant lines with heavy fruits or high solid content should be increased moderately.
3. If a colony variety is grown in areas with serious diseases, the amount of seeds of plant lines with strong disease resistance should be increased for better resistance.
4. The ratio of mixing can be modified according to a special requirement for certain characteristics. For stability of colony varieties in characteristics, the modified amount and adjusted ratio should be recorded accurately and strictly, so that identical colony varieties can be produced in a same way in the next preparation of seeds.
5. Other colony varieties with some special characteristics or particular breeding goals can be developed from the fundamental population in a similar way as mentioned above. Scores, dozens or even hundreds of colony or group varieties with distinctive characteristics can be developed from a fundamental population.
6. The original plant lines of a colony variety in the fundamental population will be checked for identification and verification of seeds in the seed production.

Example 7

Constitution of Fundamental Populations from Descendants of Recurrent Selection and their Seed Production I. Experimental Materials—Wheat 18 high-quality, high-yielding and disease-resistant varieties were adopted as parental lines: Shaan-Nong 757, Tai TI5, JI-Shen-Cang 6001, Jin-Mai 54, Ke-Nong 9204, Yu-Mai 46, Liao-Chun 12, Shen-Mian 96, Ken-Jiu 10, Ken-Hong 14, Chi-Mai 5, Meng-Mai 30, Yang-Mai 10, Gan-Chun 20, Quan-Mai 3, Yan-Zhan 4110, Chuan-Yu 5404, Yu-Mai 7. Dwarf male sterile wheat was the recurrent line.

II. Method for Constitution of Fundamental Populations

Each of the above 18 varieties was planted in an alternate row with dwarf male sterile wheat, 10 plants a row. The hybrid seeds were picked up from dwarf male sterile wheat and 1800 plant lines from them were planted in the field next year. Meanwhile, a half-sibling hybridizations were conducted between 900 comprehensively-elite individual plants selected out of above plant lines and dwarf male sterile individual plants in the population so that a further recombination could be completed and more elite genes could be incorporated in them in the second recurrent selection. After three generations of self crossing, 400 fertile plants with comprehensively elite traits were selected. Two seeds were collected from each plant and at least 10 self-crossed plants were retained for each individual plant line, and they were self-crossed for several generations towards their stability. Finally, a total of 4000 plant lines became the fundamental population and they were numbered as XM1, XM2, XM3, XM4 . . . XM4000.

III. Method for Constitution of Colony Varieties and Seed Production

After evaluation of the fundamental population, 40 single-genotype lines with good quality, consistent growth durations and plant height were selected from 4000 plant lines of the fundamental population. After they were planted once more in the field for confirming their performance, they made up the colony variety or group variety JTXM. It included the following plant lines: XM1, XM18 (good resistance), XM31, XM44, XM57, XM59, XM88 (good resistance), XM143, XM247, XM354 (high gluten content), XM460 (low gluten content), XM567, XM776 (low gluten content), XM909 (low gluten content), XM996, XM1044, XM1097 (high gluten content), XM1112, XM1210 (good resistance), XM1213, XM1322 (high gluten content), XM1428 (good resistance), XM1634, XM1702, XM1843, XM1914, XM2017, XM2047, XM2473, XM2533, XM2551, XM2688 (good resistance), XM2908, XM3051, XM3289 (low gluten content), XM3524, XM3803, XM3890, XM3954 (high gluten content) and XM3989 (low gluten content).

Performance of colony variety JTXM: Growth duration 114 days, plant height 100 cm, crude protein content 17%.

Method for Seed Production

1. The above-mentioned 40 plant lines were multiplied separately and their seeds were then mixed in an equal ratio to form the preparation for next planting.
2. For high gluten content, the amount of seeds of plant lines with high gluten content should be increased moderately or that with low gluten content should be reduced moderately.
3. If a colony variety is grown in areas with serious diseases, the amount of seeds of plant lines with strong disease resistance should be increased for better resistance.
4. The ratio of mixing can be modified according to a special requirement for certain characteristics. For stability of colony varieties in characteristics, the modified amount and adjusted ratio should be recorded accurately and strictly, so that identical colony varieties can be produced in a same way in the next preparation of seeds.
5. Other colony varieties with some special characteristics or particular breeding goals can be developed from the fundamental population in a similar way as mentioned above. Scores, dozens or even hundreds of colony or group varieties with distinctive characteristics can be developed from a fundamental population.
6. The original plant lines of a colony variety in the fundamental population will be checked for identification and verification of seeds in the seed production.

Example 8

Constitution of Fundamental Populations from Mixtures of Descendants of Various Crosses and their Seed Production Chili Pepper I. Experimental Materials 6 parental lines of different origins were utilized in the experiment: Zhong-Jiao 6, Zhong-Jiao 5, Zhong-Jiao 11, Ning-Jiao 5, B Te-Zao, Ha-Jiao 3.

II. Method for Constitution of Fundamental Populations (Ning-Jiao 5×B Te-Zao)×Ha-Jiao 3, 500 individual plants were produced.

[(Zhong-Jiao5×Zhong-Jiao 11)×(Ning-Jiao 5×B Te-Zao)], 1000 individual plants produced at segregation generations.

The seeds collected in the above two hybridizations were all sowed in the field to acquire 1500 individual plants. In the next generation, 10 plants were grown in a row for each plant line and a total of 1500 rows were planted for all plant lines. Two seeds were collected from each plant. In later generations, at least 10 self-crossed plants were retained for each individual plant line, and they were self-crossed for several generations towards their stability. From about 15000 stable individual plants, 3000 elite plants were chosen to form the fundamental populations and they were numbered as LJ1, LJ2, LJ3, LJ4 . . . LJ3000.

III. Method for Constitution of Colony Varieties and Seed Production

After evaluation of the fundamental population, 30 single-genotype lines which were consistent in growth durations, plant height and fruit shape were selected from 3000 plant lines of the fundamental population. After they were planted once more in the field for confirming their performance, they made up the colony variety or group variety JTLJ. It included the following plant lines: 115, LJ19 (good resistance), LJ25, LJ33, LJ49, LJ51, LJ58, LJ88 (good resistance), LJ90, LJ163, LJ244, LJ356, LJ467, LJ566, LJ776 (hot), LJ896, LJ910 (hot), LJ999, LJ1096 (hot), LJ1116, LJ1218 (good resistance), LJ1313, LJ1322 (hot), LJ1528 (good resistance), LJ1534, LJ1934, LJ2702, LJ2803, LJ2908 and LJ2974.

Performance of colony variety JTLJ: Growth duration 126 days, plant height 56 cm, bull-horn fruit shape, 12% yield gain over the same grade varieties.

Method for Seed Production

1. The above-mentioned 30 plant lines were multiplied separately and their seeds were then mixed in an equal ratio to form the preparation for next planting.
2. For a hot taste, the amount of seeds of plant lines with hot taste should be increased moderately.
3. If a colony variety is grown in areas with serious diseases, the amount of seeds of plant lines with strong disease resistance should be increased for better resistance.
4. The ratio of mixing can be modified according to a special requirement for certain characteristics. For stability of colony varieties in characteristics, the modified amount and adjusted ratio should be recorded accurately and strictly, so that identical colony varieties can be produced in a same way in the next preparation of seeds.
5. Other colony varieties with some special characteristics or particular breeding goals can be developed from the fundamental population in a similar way as mentioned above. Scores, dozens or even hundreds of colony or group varieties with distinctive characteristics can be developed from a fundamental population.
6. The original plant lines of a colony variety in the fundamental population will be checked for identification and verification of seeds in the seed production.

Flowering Chinese Cabbage (*Brassica campestris* L. ssp. *Chinensis* var. *utilis* Tsen, et, Lee)

I. Experimental Materials

Listed below are the parental lines of crosses and they originate from the Guangdong province. Te-Qing-Chi-Xin 4, Chi-Xin 29 and Sui-Qing 1 of dark-green type; You-Qing 12, Si-Jiu 19, You-Qing 49, Lu-Bao 70, Qing-Bao 40 of light-green type; You-Lu 70, Chi-Xin 2, You-Qing 50 of glossy-green type; Si-Jiu-Cai-Xin of yellow-green type.

II. Method for Constitution of Fundamental Populations

Te-Qing-Chi-Xin 4×You-Qing 50; You-Qing 49×Chi-Xin 2;

Qing-Bao 40×Sui-Qing 1; Lu-Bao 70×You-Lu 70;

You-Qing 12×Si-Jiu 19; Si-Jiu-Cai-Xin×Chi-Xin 29.

50 seeds were collected from each of the above crosses at the F2 generation.

(Te-Qing-Chi-Xin 4×You-Qing 50) $F_1$×(You-Qing 49×Chi-Xin 2) $F_1$, 50 seeds were collected.

(Qing-Bao 40×Sui-Qing 1) $F_1$×(Lu-Bao 70×You-Lu 70) $F_1$, 50 seeds were collected.

(You-Qing 12×Si-Jiu 19) F$_1$×(Si-Jiu-Cai-Xin×Chi-Xin 29) F$_1$, 50 seeds were collected The seeds collected in the above hybridizations were all sowed in the field to acquire 450 individual plants. In the next generation, 10 plants were grown in a row for each plant line and a total of 450 rows were planted for all plant lines. Two seeds were collected from each plant row. In later generations, at least 10 self-crossed plants were retained for each individual plant line, and they were self-crossed for several generations towards their stability. From about 4500 stable individual plants, 2000 elite plants were chosen to form the fundamental populations and they were numbered as CX1, CX2, CX3, CX4, . . . CX2000.

III. Method for Constitution of Colony Varieties and Seed Production

After evaluation of the fundamental population, 26 single-genotype lines which were consistent in growth durations, plant height and leaf color were selected from 2000 plant lines of the fundamental population. After they were planted once more in the field for confirming their performance, they made up the colony variety or group variety JTCX. It included the following plant lines: CX5, CX19 (strong resistance), CX25, CX33, CX49, CX51, CX58, CX88 (strong resistance), CX90, CX163, CX244, CX356, CX467, CX566, CX776 (dark green), CX896, CX910 (dark green), CX999, CX1096 (dark green), CX1116, CX1218 (strong resistance), CX1313, CX1322 (dark green), CX1528 (strong resistance), CX1534 and CX1934.

Performance of colony variety JTCX: Days to initial harvest—30 days; plant height of 32 cm; 10% yield gain over the same grade varieties.

Method for Seed Production

1. The above-mentioned 26 plant lines were multiplied separately and their seeds were then mixed in an equal ratio to form the preparation for next planting.
2. For a dark—green leaf color, the amount of seeds of plant lines with dark-green leaf color should be increased moderately.
3. If a colony variety is grown in areas with serious diseases, the amount of seeds of plant lines with strong disease resistance should be increased for better resistance.
4. The ratio of mixing can be modified according to a special requirement for certain characteristics. For stability of colony varieties in characteristics, the modified amount and adjusted ratio should be recorded accurately and strictly, so that identical colony varieties can be produced in a same way in the next preparation of seeds.
5. Other colony varieties with some special characteristics or particular breeding goals can be developed from the fundamental population in a similar way as mentioned above. Scores, dozens or even hundreds of colony or group varieties with distinctive characteristics can be developed from a fundamental population.
6. The original plant lines of a colony variety in the fundamental population will be checked for identification and verification of seeds in the seed production.

Eggplant 15 varieties from the Guangdong province of China were adopted as parental lines of crosses and they had different fruit shape and color: Zi-Hei 2, Hei-Bao-Fu-Qiu-Qie, Hei-Hu-Zao-Qie of the dark-purple type; Tai-Ke-Zi-Yuan-Qie and American Hei-Jin of the dark-purple and round type; 9318 Chang-Qie, Jia-Li-Chang-Qie, Ji-Nan 94-1, Chang-Hong 2 and Long-Feng-Qie-Zi of the purple and long type; Bang-Lu-Qie and Lu-Qie 3 of the glossy-green type; Lu-Qie 1, Lu-Qie 3, Lu-Qie 4 of other type.

II. Method for Constitution of Fundamental Populations

Lu-Qie 1×Lu-Qie 3, 50 seeds were collected at F2 generations;

(Lu-Qie 3×Lu-Qie 4)×Lu-Qie 3, 50 seeds were collected;

(Hei-Hu-Zao-Qie×Lu-Qie 1) F$_1$×(Lu-Qie 3×Lu-Qie 4) F$_1$, 50 seeds were collected;

(Zi-Hei 2×Lu-Qie 3) F$_1$×(American Hei-Jin×Bang-Lu-Qie) F$_1$, 50 seeds were collected;

(Ji-Nan 94-1×Hei-Hu-Zao-Qie) F$_1$, ×(Jia-Li-Chang-Qie× Chang-Hong 2) F$_1$, 50 seeds were collected;

(9318 Chang-Qie×Tai-Ke-Zi-Yuan-Qie) F$_1$×(Long-Feng-Qie-Zi×Hei-Bao-Fu-Qiu-Qie) F$_1$, 50 seeds were collected;

[(Zi-Hei 2×Lu-Qie 3) F$_1$×(American Hei-Jin×Bang-Lu-Qie) F$_1$] F$_1$×[(Ji-Nan 94-1×Hei-Hu-Zao-Qie) F$_1$×(Jia-Li-Chang-Qie×Chang-Hong 2) F$_1$] F$_1$, 50 seeds were collected;

[(Zi-Hei 2×Lu-Qie 3) F$_1$×(American Hei-Jin×Bang-Lu-Qie) F$_1$] F$_1$×[(9318 Chang-Qie×Tai-Ke-Zi-Yuan-Qie) F$_1$× (Long-Feng-Qie-Zi×Hei-Bao-Fu-Qiu-Qie) F$_1$] F$_1$—male 2}, 50 seeds were collected.

The seeds collected in the above hybridizations were all sowed in the field to acquire 400 individual plants. In the next generation, 10 plants were grown in a row for each plant line and a total of 2000 rows were planted for all plant lines. Two seeds were collected from each plant. In later generations, at least 10 self-crossed plants were retained for each individual plant line, and they were self-crossed for several generations towards their stability. From about 4000 stable individual plants, 2000 elite plants were chosen to form the fundamental populations and they were numbered as QZ1, QZ2, QZ3, QZ4, . . . QZ2000.

III. Method for Constitution of Colony Varieties and Seed Production

After evaluation of the fundamental population, 24 single-genotype lines which were consistent in growth durations, plant height and fruit color were selected from 2000 plant lines of the fundamental population. After they were planted once more in the field for confirming their performance, they made up the colony variety or group variety JTQZ. It included the following plant lines: QZ9, QZ20 (strong resistance), QZ27, QZ36, QZ49, QZ56, QZ58, QZ89 (strong resistance), QZ94, QZ154, QZ245, QZ353, QZ467, QZ569, QZ896, QZ910, QZ989, QZ1216, QZ1202 (strong resistance), QZ1413, QZ1521, QZ1728 (strong resistance), QZ1834 and QZ1934.

12 pairs of lines from 24 above-selected single-genotype lines could also be matched to become combinations so that their heterosis could be utilized in the production.

Performance of colony variety JTQZ: Days to initial harvest—102 days; plant height of 75 cm; 15% yield gain over the same grade varieties.

Method for Seed Production

1. The above-selected 24 plant lines were multiplied separately. Their seeds or the seeds of their 12 hybrid combinations were then mixed in an equal ratio to form the preparation for next planting.
2. If a colony variety is grown in areas with serious diseases, the amount of seeds of plant lines with strong disease resistance should be increased for better resistance.
3. The ratio of mixing can be modified according to a special requirement for certain characteristics. For stability of colony varieties in characteristics, the modified amount and adjusted ratio should be recorded accurately and strictly, so that identical colony varieties can be produced in a same way in the next preparation of seeds.

4. Other colony varieties with some special characteristics or particular breeding goals, such as round or long fruit shape can be developed from the fundamental population in a similar way as mentioned above. Scores, dozens or even hundreds of colony or group varieties with distinctive characteristics can be developed from a fundamental population.

5. The original plant lines of a colony variety in the fundamental population will be checked for identification and verification of seeds in the seed production.

Cabbage Mustard

I. Experimental Materials

Different series of cabbage mustard including 12 varieties were adopted as parental lines of crosses. Xiang-Gang-Bai-Hua-Jie-Lan, Xi-Ye-Zao-Jie-Lan, Zhou-Ye-Zao-Jie-Lan of early-maturing type; Tai-Wang-Zhong-Hua, Zhong-Chi-Jie-Lan, Xiang-Gang-Zhong-Hua, He-Tan-Jie-Lan and Zhong-Hua-Jie-Lan of medium-maturing type; Zhou-Ye-Chi-Jie-Lan, Dong-Fang-Dian-Jie-Lan, Pu-Tong-Jie-Lan-1, Chi-Hua-Jie-Lan of late-maturing type.

II. Method for Constitution of Fundamental Populations

Zhong-Chi-Jie-Lan×Pu-Tong-Jie-Lan-1, 60 seeds were collected at F2 generation;

(Xiang-Gang-Bai-Hua-Jie-Lan×Xi-Ye-Zao-Jie-Lan)× Zhou-Ye-Zao-Jie-Lan, 60 seeds were collected;

(Pu-Tong-Jie-Lan-1×Dong-Fang-Jian-Jie-Lan) $F_1$× (Xiang-Gang-Bai-Hua-Jie-Lan×Xi-Ye-Zao-Jie-Lan) $F_1$, 60 seeds were collected;

(Xiang-Gang-Bai-Hua-Jie-Lan×Pu-Tong-Jie-Lan-1) $F_1$× (Xiang-Gang-Zhong-Hua×Dong-Fang-Jian-Jie-Lan) $F_1$, 50 seeds were collected;

(Chi-Hua-Jie-Lan×Zhou-Ye-Zao-Jie-Lan) $F_1$×(He-Tan-Jie-Lan×Zhou-Ye-Chi-Jie-Lan) $F_1$, 550 seeds were collected;

(Tai-Wang-Zhong-Hua×Zhong-Chi-Jie-Lan) $F_1$×(Zhong-Hua-Jie-Lan×Xi-Ye-Zao-Jie-Lan) $F_1$, 60 seeds were collected.

The seeds collected in the above hybridizations were all sowed in the field to acquire 340 individual plants. In the next generation, 10 plants were grown in a row for each plant line and a total of 340 rows were planted for all plant lines. Two seeds were collected from each plant. In later generations, at least 10 self-crossed plants were retained for each individual plant line, and they were self-crossed for several generations towards their stability. From about 3400 stable individual plants, 1800 elite plants were chosen to form the fundamental populations and they were numbered as JL1, JL2, JL3, JL4, JL1800.

III. Method for Constitution of Colony Varieties and Seed Production

After evaluation of the fundamental population, 20 single-genotype lines which were consistent in growth durations, plant height and leaf color were selected from 1800 plant lines of the fundamental population. After they were planted once more in the field for confirming their performance, they made up the colony variety or group variety JTJL. It included the following plant lines: JL9, JL20 (strong resistance), JL27, JL49, JL56, JL58, JL89 (strong resistance), JL154, JL245, JL353, JL467, JL569, JL896, JL910, JL1216, JL1202 (strong resistance), JL1413, JL1521 and JL1728 (strong resistance).

Performance of colony variety JTJL: Days to initial harvest—38 days, plant height of 30 cm, 20% yield gain over the same grade varieties.

Method for Seed Production

1. The above-selected 20 plant lines were multiplied separately, and their seeds were then mixed in an equal ratio to form the preparation for next planting.

2. If a colony variety is grown in areas with serious diseases, the amount of seeds of plant lines with strong disease resistance should be increased for better resistance.

3. The ratio of mixing can be modified according to a special requirement for certain characteristics. For stability of colony varieties in characteristics, the modified amount and adjusted ratio should be recorded accurately and strictly, so that identical colony varieties can be produced in a same way in the next preparation of seeds.

4. Other colony varieties with some special characteristics or particular breeding goals can be developed from the fundamental population in a similar way as mentioned above. Scores, dozens or even hundreds of colony or group varieties with distinctive characteristics can be developed from a fundamental population.

5. The original plant lines of a colony variety in the fundamental population will be checked for identification and verification of seeds in the seed production.

Example 9

Constitution of Fundamental Populations in Asexually-Propagated Crops and their Seed Production I. Experimental Materials—Potato Zhong-shu 3, Zhong-shu 4, Chun-shu 3, Chun-shu 4, An-shu 56, Chuan-yu-zao, Ning-shu 5, Qing-shu 168, Zao-Da-Bai.

II. Method for Constitution of Fundamental Population (Zhong-shu 3×Chun-shu 4)×Chuan-yu-zao, 600 hybrid seeds were collected;

(Zhong-shu 4×Chun-shu 3)×An-shu 56, 600 hybrid seeds were collected;

(Ning-shu 5×Qing-shu 168)×Zao-Da-Bai, 600 hybrid seeds were collected.

The seeds collected in the above hybridizations were all sowed in the field to acquire 1800 asexually-propagated lines. They directly made up the fundamental population and were numbered as MLS1, MLS2, MLS3, MLS4 . . . MLS1800.

III. Method for Constitution of Colony Varieties and Seed Production

After evaluation of the fundamental population, 12 single-genotype lines with consistent growth durations and plant height were selected from 1800 clone lines of the fundamental population. After they were planted once more in the field for checking their performance, they made up the colony variety or group variety JTMLS. It included the following clone lines: MLS20 (strong resistance), MLS59, MLS89 (strong resistance), MLS158, MLS245, MLS353, MLS569, MLS896, MLS1256 (strong resistance), MLS1416, MLS1565 and MLS1798 (strong resistance).

Performance of colony variety JTMLS: Growth duration of 95 days, plant height of around 75 cm, 27% gain in yield compared to potato varieties with similar growth duration.

Method for Potato Seed Stock Production

1. The above-selected 12 clone lines were multiplied separately and their potato seed stock were then mixed in an equal ratio to form the preparation for next planting.

2. If a colony variety is grown in areas with serious diseases, the amount of potato seed stock of clone lines with strong disease resistance should be increased for better resistance.

3. The ratio of mixing can be modified according to a special requirement for certain characteristics. For stability of colony varieties in characteristics, the modified amount and adjusted ratio should be recorded accurately and strictly, so that identical colony varieties can be produced in a same way in the next preparation of potato seed stock.

4. Other colony varieties with some special characteristics or particular breeding goals can be developed from the fundamental population in a similar way as mentioned above. Scores, dozens or even hundreds of colony or group varieties with distinctive characteristics can be developed from a fundamental population.

5. The original clone lines of a colony variety in the fundamental population will be checked for identification and verification in the potato seed stock production.

The invention claimed is:

1. A method for constitution and production of multi-genotype colony varieties of a crop, comprising:
    a) selecting 3 or more parental lines of a crop according to at least one breeding goal selected from the group consisting of quality, yield, and resistance to pests and diseases, wherein the selection of a parental line varies according to the breeding goal;
    b) crossing the 3 or more parental lines with each other to form hybrids of the 3 or more parental lines;
    c) self-crossing the hybrids for a sufficient number of generations for the progeny of the self-crosses to undergo segregation and recombination to form a fundamental population of stable single-genotype lines, wherein each stable single-genotype line is genetically distinct from the other stable single-genotype lines in the population;
    d) characterizing the uniformity of each stable single-genotype line for selection, by evaluating growth duration and plant height of each stable single-genotype line;
    e) selecting, from the fundamental population, stable single-genotype lines that are uniform in growth duration and plant height, and share at least one trait suitable for the at least one breeding goal, thereby forming a colony variety;
    f) multiplying each stable single-genotype line in the colony variety separately to evaluate uniformity;
    g) eliminating from the colony variety any stable single-genotype line that is not uniform in growth duration and plant height, and share at least one trait suitable for the at least one breeding goal; and
    h) according to the at least one breeding goal, mixing seeds of each stable single-genotype line in the colony variety in a specific ratio to form preparations for planting, thereby forming the multi-genotype colony variety of the crop, wherein the multi-genotype colony variety exhibits commercial viability.

2. The method according to claim 1, wherein at least one stable single-genotype line in the colony variety is selected from the progeny of single crosses, double crosses, triple crosses, composite crosses, or back crosses.

3. The method according to claim 1, wherein the stable single-genotype lines of the fundamental population are generated from one or more method selected from the group consisting of:
    a) composite crosses including single, double, triple and recurrent crosses;
    b) crosses utilizing various gene introgression lines;
    c) crosses utilizing descendants of various recurrent selections;
    d) utilizing $F_1$ hybrid combinations as fundamental populations;
    e) utilizing one or more stable single-genotype progeny plants produced by the methods of any one of a-d as a fundamental population; and
    f) for asexually-propagated crops, clonal lines produced by the methods of any one of a-e are adopted as a fundamental population.

4. The method according to claim 1, wherein the crop is selected from the group consisting of self-pollinating crops, often-cross-pollinating crops, and asexually-propagated crops.

5. The method according to claim 4, wherein the self-pollinating crops include rice, peanut, wheat, soybean or tomato.

6. The method according to claim 4, wherein the often-cross-pollinating crops include rape, cotton, chili pepper, flowering Chinese cabbage (*Brassica campestris* L. ssp. *Chinensis* var. *utilis* Tsen, et, Lee), eggplant or cabbage mustard.

7. The method according to claim 4, wherein the asexually-propagated crops include potato, sweet potato, pitahaya, rose or camellia.

8. The method according to claim 1, wherein the colony variety comprises 2 to 10,000 genotypes.

9. The method according to claim 1, wherein the genetic diversity within the colony variety is detected by polymorphisms in molecular markers.

10. The method according to claim 1, further comprising generating single-genotype conventional varieties from the multi-genotype colony variety by pedigree selection or asexual propagation.

11. The method according to claim 1, wherein the number of parental lines ranges from 3 to 10,000.

* * * * *